United States Patent [19]

Gregory et al.

[11] Patent Number: 4,820,690

[45] Date of Patent: Apr. 11, 1989

[54] DUODENAL AND GASTRIC ULCER TREATMENT WITH ORAL UROGASTRONE

[75] Inventors: Harold Gregory, Macclesfield; Keith G. McCullagh, Princes Risborough, both of United Kingdom

[73] Assignee: G. D. Searle & Co., Chicago, Ill.

[21] Appl. No.: 69,550

[22] Filed: Jul. 2, 1987

Related U.S. Application Data

[63] Continuation of Ser. No. 723,978, Apr. 16, 1985, abandoned.

[30] Foreign Application Priority Data

Apr. 17, 1984 [GB] United Kingdom ............... 8409960

[51] Int. Cl.⁴ .............................................. A61K 37/24
[52] U.S. Cl. .................................... 514/12; 514/925; 514/926
[58] Field of Search ............... 530/324; 514/925, 926, 514/12

[56] References Cited

U.S. PATENT DOCUMENTS

| | | | |
|---|---|---|---|
| 3,883,497 | 5/1975 | Gregory et al. | 530/834 |
| 4,032,633 | 6/1977 | Gregory et al. | 514/12 |
| 4,035,485 | 7/1977 | Gregory et al. | 514/9 |

FOREIGN PATENT DOCUMENTS 0161817 11/1985 European Pat. Off. .
0161816 11/1985 European Pat. Off. .

OTHER PUBLICATIONS

HORI, et al., Effect of Bile Salts and Oil-in Water Emulsions on the Intestinal Absorption of Urogastrone in the Rat, Chem. Pharm. Bull., 25, 1974–1979 (1977).
Luccetti et al., Antiulcer Action of Urogastrone, Boll. Chim. Farm. 112(8) 532 (1973).
Gregory et al., The Identification of Urogastrone in Serum, Saliva and Gastric Juice, Gastronterology, 77, 313–318 (1973).
The Merck Index, 10th Edition p. 3496–7 (1983).
Gregory H., Isolation and Structure of Urogastrone and its Relationship to Epidermal Growth Factor, Nature, 257, 325–327 (1975).

*Primary Examiner*—Johnnie R. Brown
*Assistant Examiner*—Jacqueline M. Stone
*Attorney, Agent, or Firm*—Mary Jo Kanady; Paul Matukaitis

[57] ABSTRACT

Pharmaceutical compositions for oral administration comprise human urogastrone or a urogastrone fragment as active ingredient and such an active ingredient may be used for the manufacture of a medicament for promoting healing of a damaged alimentary tract.

5 Claims, No Drawings

DUODENAL AND GASTRIC ULCER TREATMENT WITH ORAL UROGASTRONE

This case is a continuation of Ser. No. 06/723,978 filed 4-16-85, now abandoned.

The present invention relates generally to human urogastrone and related polypeptides and in particular to their use in promoting healing of a damaged alimentary tract and in the manufacture of an orally administrable medicament therefor as well as to pharmaceutical compositions for oral administration which comprise human urogastrone or a related polypeptide as active ingredient. The human urogastrone is preferably recombinant derived beta-urogastrone produced by microbial methods and is of particular interest in the treatment of duodenal and gastric ulcers.

Urogastrone is a polypeptide hormone (protein) synthesized in the salivary glands and duodenal Brunner's glands of normal humans (see for example Heitz et al, Gut, 19: 408, 1978). Urogastrone is known (see for example Elder et al, Gut 16: 887, 1975 and Koffman et al, Gut 23: 951, 1982) to inhibit acid secretion in the stomach of humans when administered by a systemic route.

Urogastrone was first identified and described in 1939 (by Gray et al, Science, 89: 489, 1939) as a component in human urine which inhibits gastric (stomach) acid secretion in experimental animals when given parenterally. This component, named "urogastrone", was completely sequenced and its structure published in 1975 (Gregory, Nature (Lond.) 247: 325, 1975). Urogastrone is probably synthesized in man as part of a larger "pro-peptide" molecule from which it is cleaved by specific proteases to liberate the active form of the protein (Frey et al, Proc. Nat. Acad. Sci, USA, 76: 6294, 1979). This active form of urogastrone, composed of 53 amino acids is known as beta-urogastrone. Further degradative cleavage in the body yields a slightly smaller form of the protein of 52 amino acids known as gamma-urogastrone which is also found in human urine and which only differs from beta-urogastrone in lacking the carboxy-terminal arginine residue (see for example, Gregory and Preston, Int. J. Peptide Prot. Res. 9: 107, 1977). Both polypeptides have equal activity in inhibiting acid secretion when administered intravenously to animals (see for example UK Pat. No. 1,394,846). Other urogastrone species produced by further enzymatic cleavage having for example example only amino acids 1-47 and 1-46 are also known to inhibit acid secretion when administered by intravenous or subcutaneous routes (see for example British Pat. Nos. 1,461,105 and 1,461,106).

A related polypeptide called epidermal growth factor (mEGF) has been isolated and characterised from mouse salivary glands (Cohen, J. Biol. Chem., 237: 1555, 1962). mEGF consists of a polypeptide of 53 amino acids which resembles beta-urogastrone but differs in detailed amino acid sequence. Mouse EGF is known to have similar biological activities to urogastrone in inhibiting gastric acid secretion and is known to stimulate the proliferation of epithelial tissue (see for example UK Pat. No. 1,417,776 and Carpenter and Cohen, Ann. Rev. Biochem, 48: 193, 1979).

In addition to their antisecretory properties, urogastrone and mouse EGF are known to protect the gastro-intestinal mucosa of animals against damaging stimuli and ulcer formation when administered concurrently with or prior to the injurious stimuli (see for example Kirkegaard et al, Gastroenterology 85: 1277, 1983 and Konturek et al, Gut 22: 927, 1981). This "cytoprotective" effect is known to occur when the polypeptides are administered parenterally at doses below that necessary to cause inhibition of acid secretion. Cytoprotection has also been observed when the polypeptides are administered directly into the gastro-intestinal lumen from where absorption into the blood stream does not occur and from where acid secretion is not inhibited (see for example Kirkegaard et al, Gastroenterology 85: 1277, 1983 cited above). However, there is no evidence that urogastrone or mEGF administered orally or into the gastro-intestinal lumen can stimulate gastro-intestinal epithelial cell proliferation.

The present invention relates to the discovery that urogastrone will promote the healing of damaged tissues of the alimentary tract such as for example ulcers of the mucosa and submucosa of the gastrointestinal tract when administered orally or into the gastrointestinal lumen after the ulcer has formed. This effect is unexpected since it is shown that urogastrone at high doses infused into the stomach lumen has no effect on the rate of gastrointestinal cell proliferation and growth. It is also shown that urogastrone administered orally does not inhibit acid secretion and, of course, cytoprotection is unable to account for an increased rate of healing after the ulcer has formed.

According to the present invention there is provided the use of human urogastrone or a urogastrone fragment for the manufacture of an orally administrable medicament for promoting healing of a damaged alimentary tract of a mammal. The orally administrable medicament is preferably for promoting gastrointestinal ulcer healing, especially the healing of duodenal ulcers.

According to a further feature of the present invention there is provided a method of promoting healing of a damaged alimentary tract of a mammal which comprises the oral administration of human urogastrone or a urogastrone fragment to said mammal. The method of the present invention is of particular interest in promoting gastrointestinal ulcer healing, especially duodenal ulcer healing.

According to a further feature of the present invention there is provided an agent for promoting the healing of a damaged alimentary tract in an orally ingestible form which comprises human urogastrone or a urogastrone fragment as active ingredient in association with a pharmaceutical carrier or excipient. The agent is preferably for promoting the healing of gastrointestinal ulcers, especially duodenal ulcers.

According to a still further feature of the present invention there is provided a pharmaceutical composition for oral administration which comprises human urogastrone or a urogastrone fragment as active ingredient in association with a pharmaceutical carrier or excipient.

Urogastrone per se having the amino acid sequence and structure defined by Gregory H. in Nature (Lond,) 247: 325, 1975 (beta-urogastrone) is preferably used. If desired however a urogastrone fragment capable of promoting the healing of gastrointestinal ulcers may be used. Such a fragment may for example be a polypeptide comprising only amino acids 1-46, 1-47, 1-48, 1-49, 1-50, 1-51 or 1-52. It will be appreciated that references herein to urogastrone or a urogastrone fragment include such polypeptides which carry a methionine or formyl-methionine at their N-termini as well as such polypeptides which carry a peptide sequence of up to 12 amino acid residues at their N-termini, which sequence may in turn be preceded by methionine or formylmethionine, providing that the total number of amino acid residues in the sequence of amino acid residues preceding the N-terminus does not exceed 12.

Human urogastrone or a urogastrone fragment may if desired be used as the sole growth factor or may be used in combination with other growth factors such as (1) those transforming growth factors which compete with human urogastrone for receptor binding and which do not require human urogastrone for the induction of colony formation in soft agar; (2) those transforming growth factors which do not compete with urogastrone for receptor binding and which do not require urogastrone for colony formation in soft agar; and (3) those transforming growth factors which both compete for urogastrone receptors and require urogastrone for colony formation in soft agar.

While we do not wish to be bound by theoretical considerations it is considered that urogastrone promotes healing by stimulating those normal cells adjacent to the damaged tissue. It will therefore be appreciated that the degree of healing which the oral administration of human urogastrone or urogastrone fragment is able to promote will be dependent on the relationship between the area of damaged tissue and the adjacent normal tissue. The present invention is thus of particular interest in promoting the healing of localised areas of damaged tissue such as gastrointestinal ulcers. Human urogastrone or a urogastrone fragment is also of potential interest, however, for example as a restorative in relation to the gastrointestinal effects of anticancer cytotoxic drugs, but it will be appreciated that where the area of damaged tissue is substantially increased in relation to the adjacent normal tissue the ability of human urogastrone or a urogastrone fragment to promote healing will be correspondingly reduced.

Urogastrone and mEGF are present in mammalian tissues and fluids in amounts too small to provide a source of the proteins for human clinical use and the polypeptides are too large to be readily produced by conventional peptide chemical synthesis. However, beta-urogastrone is known to be capable of production from a synthetic oligonucleotide gene expressed in microbial cells and the expressed protein can thence be recovered (see for example, European Patent Publication No. 46039 and also Sassenfeld and Brewer, Biotechnology 2: 76, 1984).

The oral pharmaceutical composition may be formulated by means known to the art into the form of, for example, aqueous or oily solutions or suspensions, emulsions, tablets, capsules, lozenges, chewing gums or dispersible powders.

A preferable oral pharmaceutical composition is one suitable for administration in unit dosage form, for example an aqueous or oily solution or suspension or an emulsion containing between 0.01 mg. and 10 mg., preferably 0.1 to 1 mg., of urogastrone or urogastrone fragment per 5 ml., or a composition of unit dosage form, for example a tablet, capsule, lozenge or stick of chewing gum each containing between 0.01 mg. and 10 mg. preferably 0.1 to 1 mg., of urogastrone or urogastrone fragment.

The oral pharmaceutical composition will be administered to a mammal for the treatment of a damaged alimentary tract so that each patient will receive an oral dose of between 0.1 and 100 µg/kg/day. A preferred dose range is between 1 and 100 µg/kg/day, and a particularly preferred range is between 1 and 10 µg/kg/day. The composition may be administered 1 to 4 times, and preferably once, per day and will preferably be admininstered before food, for example about an hour before food.

The invention is exemplified by experiments in rats in which duodenal ulcers similar to human duodenal ulcers are induced by the subcutaneous administration of sufficient amounts of the toxic agent, cysteamine. Five to seven days after formation of the duodenal ulcers, groups of rats are treated with repeated aqueous solutions of purified beta-urogastrone, either by adding the treatment solution to the drinking water or by administration of the solution by oral gavage, the treatment being given daily over periods of 20 to 50 days. Similar groups of rats with cysteamine induced ulcers are given identical oral doses of a control solution containing no urogastrone. At the end of the treatment period, the number of healed and unhealed ulcers are counted in each group of rats. Significantly higher percentages of healed ulcers are shown to occur in rats treated with oral beta-urogastrone than in rats receiving control solutions.

The invention is also exemplified by experiments in which groups of rats with cysteamine-induced ulcers are treated orally with cimetidine, an antisecretory agent, in amounts sufficient to inhibit gastric acid secretion and in which similar groups of rats are treated orally with doses of beta-urogastrone. A similar percentage of healed ulcers is shown to occur in rats receiving the beta-urogastrone compared to rats receiving cimetidine.

The invention is also exemplified by experiments in beagle dogs prepared with Heidenhain pouches in their stomachs in which recombinant beta-urogastrone is administered as intravenous or intragastric bolus doses and effects on histamine stimulate acid secretion monitored. Whereas intravenous administration of low doses of urogastrone is shown to inhibit gastric acid secretion, oral administration of similar or much larger doses is shown to have no effect. These results show that the mechanism of enhanced ulcer healing following oral treatment with urogastrone is not by inhibition of acid secretion which is a known property of urogastrone but by some other local gastrointestinal mechanism.

The invention is also exemplified by the results in which gastrointestinal epithelial proliferation rates are measured in rats maintained on parenteral nutrition but administered recombinant derived beta-urogastrone by intravenous or intragastric infusion. Whereas intravenous infusion of low doses of urogastrone is shown to stimulate gastrointestinal epithelial proliferation, intragastric infusion of similar or much larger doses of urogastrone is shown to have no effect on gastrointestinal epethelial proliferation. These results show that the promotion of ulcer healing in the intravenous experiments is unassociated with and unexplained by stimulation of epithelial proliferation when urogastrone is administered by the oral route.

There has been a need for an antiulcer treatment which promotes the healing of damaged tissue in the alimentary tract. Uncertainty existed that urogastrone would stimulate healing; that urogastrone could penetrate to the sites of ulcer healing in the gastrointestinal tract; that repair tissue would respond to local urogastrone and that the effect would result in improved ulcer healing. Only with the production of large quantities of pure urogastrone by recombinant DNA processes could such testing take place. The results of such testing are contained in the following examples.

EXAMPLE 1. Healing of duodenal ulcers by urogastrone added to drinking water for 50 days Rats with perforating duodenal ulcers confirmed by laparotomy were selected from a large number and given two doses of cysteamine as described in the following protocol. These animals were randomly assigned to treatment groups of 15 rats each.

The protocol utilises 2 doses of cysteamine (300 mg./kg. and 150 mg./kg., 6 hours apart). This procedure produces deep perforating duodenal ulcers in a majority of the rats injected. The "chronic" ulcers heal extremely slowly. Previous studies have shown that after 50 days only 20% have healed as judged by reepithelialization of the surface. Even after 200 days, 36% remain unhealed.

In order to provide for a reliable experimental protocol, rats given 2 doses of cysteamine are subjected to an intra-abdominal inspection by laparotomy 5 days after induction. Only those rats in which perforation of the ulcer to the duodenal external serosal surface has occurred are included in the experimental groups. Rats with non-perforating ulcers are discarded. Therapy by drug or placebo then begins on day 7 post-induction. On termination after a standardised period of (21 to 50 days) therapy the duodenum is removed from all rats, fixed and stained with PAS and the number of healed and unhealed ulcers determined by macroscopic examination of the mucosal surface with a stereomicroscope. Healing is defined as restoration of complete mucosal integrity by reepithelialisation of the surface. This is confirmed by subsequent histology.

In this example, therapy commenced on day 7 following cysteamine and continued for 50 days. Treatment groups were as follows:
Group I: Control—no treatment
Group II: Urogastrone—6 µg./rat/day in drinking water
Group III: Cimetidine postitive control—100 mg./rat/day in drinking water The numbers of healed and unhealed ulcers in each group were as follows:

| Group | Treatment | n | Healed | Unhealed | Percentage Rate |
|---|---|---|---|---|---|
| I | None (negative control) | 15 | 2 | 13 | 13% |
| II | Urogastrone | 15 | 6 | 8 | 43% |
| III | Cimetidine (positive control) | 15 | 6 | 9 | 40% |

These results show that oral urogastrone treatment enhances the healing of experimental duodenal ulcers in the rat. Cimetidine administered orally at a dose sufficient to inhibit acid secretion also results in enhanced ulcer healing compared to no treatment, as it does in human peptic ulcer therapy.

EXAMPLE 2. Enhanced healing of duodenal ulcers following administration of urogastrone by oral gavage for 20 days.

In this Example the same protocol was followed as in Example 1 but therapy was continued for only 21 days after commencing on day 7 following ulcer induction. In this example the method of oral dosing was also different, recombinant beta-urogastrone being given at intervals of 8 hours, three times a day, at 10 µg./rat/dose by oral gavage in an aqueous solution of 1 ml. volume. Two groups of rats were employed, the first treated as described and the second being a control group administered 1 ml. water without urogastrone at intervals of 8 hours three times a day.

In this example the number of rats in each group with healed and unhealed ulcers were assessed blind (that is, without information on which animals had been treated and which had not) by 2 observers. The results of this assessment were as follows:

| Group | Treatment | n | Healed (1) | Healed (2) | Unhealed (1) | Unhealed (2) | Percentage healed (1) | Percentage healed (2) |
|---|---|---|---|---|---|---|---|---|
| | Observers: | | | | | | | |
| I | Urogastrone by gavage | 22 | 8 | 5 | 14 | 17 | 36% | 23% |
| II | Water only by gavage | 23 | 3 | 2 | 20 | 21 | 13% | 9% |

Both observers recorded scores which indicate that oral urogastrone treatment enhances the healing of experiment duodenal ulcers in the rat, after a treatment period in this example of only 21 days.

EXAMPLE 3. Oral administration of urogastrone at high doses does not inhibit acid secretion.

In this example, oral administration of solutions of recombinant beta-urogastrone is shown to have no effect on gastric acid secretion in dogs with Heidenhain pouches whereas intravenously administered urogastrone and mEGF inhibited acid secretion.

Male beagle dogs (14–22 kg.) were prepared with isolated Heidenhain (vagal denervated) pouches derived from the fundic area of the stomach by the method of Rudick et al, J. Surg. Res. 7: 383, 1967. Animals were allowed 4–6 weeks to recover from surgery and given a 2–3 month training period to standardise laboratory behaviour and secretory responses. The dogs were fasted for 23 hours prior to use, the pouch then flushed with warm water and histamine infused subcutaneously at a rate of 10 µg./min. Pouch secretions were collected every 15 minutes, their volume measured and aliquots titrated to pH 7.0 with 100 mM NaOH. Urogastrone solutions were administered either intravenously via a cephalic foreleg vein or orally once a secretory plateau had been attained and secretion was monitored for a further 3 hours.

Following an intravenous bolus dose of urogastrone, rapid inhibition of the acid secretion response to histamine occurred, peak inhibition being achieved within 30 minutes of urgoastrone injection. Dose response studies gave log-linear dose response regression plots from which the dose required to produce a 50% inhibition of acid secretion was calculated as 0.27 µg./kg. Recombinant beta-urogastrone, administered to the same dogs as a single oral solution dose had no effect on acid secretion even when given at doses of 4 mg. (approximately 200 µg./kg.).

This experiment shows that urogastrone is unable to inhibit gastric acid secretion when administered orally, presumably because local action of urogastrone in the stomach is unable to influence acid secretion and because urogastrone is not absorbed to any extent from the small intestine. The effect of urogastrone in causing an increased rate of ulcer healing when given orally is therefore not a reflection of the known acid secretion inhibiting property of the polypeptide and is therefore surprising.

EXAMPLE 4. Parenteral administration of urogastrone has trophic effects on the gastrointestinal mucosa.

In order to examine the pharmacological properties of recombinant urogastrone on cell proliferation and turnover in the gastro-intestinal tract, experiments were conducted using techniques for accurately measuring the changes in production rates of the gut epithelium.

Measurements of kinetic parameters associated with the turnover of gastro-intestinal epithelium in vivo are normally difficult to interpret since epithelial activity is very sensitive to alterations in food intake and passage time in the gut. In evaluating recombinant beta-urogastrone for effects on gut epithelial cells this difficulty may be circumvented by designing experiments in rats fed by total parenteral nutrition (TPN). These animals have permanent indwelling i.v. catheters connected to infusion pumps via 360° swivel joints which allow normal mobility of the rats within their cages. A complete parenteral food mixture is infused through the catheters at a rate of 60 ml./rat/24 h. The animals are allowed water in the normal way but no food by mouth. Without the stimulus of luminal food in the gut the gastrointestinal mucosa undergoes atrophy and epithelial cell division declines to a stable basal level. In this situation the direct response to urogastrone may be quantitated accurately.

Epithelial cell turnover in these experiments was determined as the crypt cell production rate (CCPR) at each site examined. CCPR was defined as the number of new cells produced per mucosal crypt per hour (for method of determination see Al Nafussi and Wright, Virch. Arch. Cell Pathol. 40: 63, 1982).

In this example the ability of recombinant urogastrone to prevent the reduction in CCPR when rats were transferred to TPN was tested, urogastrone being infused as part of the TPN solution at a concentration of 250 ng./ml. This resulted in an infusion rate of 0.65 $\mu$g. urogastrone/rat/hour (approximately 3 $\mu$g./kg./h). Infusion was continued for 10 days. The CCPR at each of 6 sites in the gastro-intestinal tract after 10 days of TPN, with and without urogastrone is shown in the following table.

| TISSUE<br>*Site<br>(n = 7) (n = 10) | CRYPT CELL PRODUCTION RATE (cells/crypt/hour) | | |
|---|---|---|---|
| | Control Group P | Urogastrone Group | Statistical significance |
| 1. Stomach | 0.10 + 0.24 | 2.00 + 0.57 | <0.01 |
| 2. Small intestine 10%* | 8.82 + 1.16 | 14.80 + 1.95 | <0.02 |
| 3. Small intestine 50%* | 7.54 + 1.14 | 20.14 + 2.73 | <0.001 |
| 4. Small intestine 90%* | 5.44 + 1.55 | 12.19 + 2.11 | <0.05 |
| 5. Colon 50% | 4.22 + 1.61 | 11.29 + 3.08 | <0.1 |
| 6. Colon 90% | 2.37 + 2.54 | 18.14 + 4.21 | <0.01 |

*The percentage figures shown refer to the exact site of measurement, determined as the percentage of the full small intestinal or colonic length, measured from the proximal end.

The data shows that urogastrone administration resulted in an enhancement of crypt cell proliferation at every site in the gastro-intestinal tract examined. The differences between urogastrone treated and control untreated animals are substantial and all reach statistical significance at the $p<0.05$ level. This experiment confirms a known property of urogastrone to stimulate cell proliferation and shows that the gastrointestinal epithelium is a target for this action when urogastrone is administered by parenteral infusion.

We claim:

1. A method of promoting the healing of duodenal and gastric ulcers in a mammal without inhibiting gastric acid secretion which comprises orally administering to said mammal an amount of beta-urogastrone or a urogastrone fragment selected from the group consisting of
a polypeptide comprising amino acids 1-46 of urogastrone,
a polypeptide comprising amino acids 1-47 of urogastrone,
a polypeptide comprising amino acids 1-48 of urogastrone,
a polypeptide comprising amino acids 1-49 of urogastrone,
a polypeptide comprising amino acids 1-50 of urogastrone,
a polypeptide comprising amino acids 1-51 of urogastrone,
a polypeptide comprising amino acids 1-52 of urogastrone;
wherein said amount is effective to promote the healing of duodenal and gastric ulcers in mammals without inhibiting gastric acid secretion.

2. A method as claimed in claim 1 wherein the beta-urogastrone or urogastrone fragment is orally administered to a mammal having its alimentary tract afflicted with a gastrointestinal ulcer.

3. A method as claimed in claim 1 wherein the beta-urogastrone or urogastrone fragment is orally administered to a mammal having its alimentary tract afflicted with a duodenal ulcer.

4. A method as claimed in claim 1 wherein between 0.1 and 100 $\mu$g./kg./day of beta-urogastrone or a urogastrone fragment is administered to said mammal.

5. A method as claimed in claim 1 wherein human beta-urogastrone is administered to said mammal.

* * * * *

Disclaimer and Dedication 4,820,690.—*Harold Gregory*, Macclesfield; *Keith G. McCullagh*, Princes Risborough, both of United Kingdom. DUODENAL AND GASTRIC ULCER TREATMENT WITH ORAL UROGASTRONE. Patent dated April 11, 1989. Disclaimer and Dedication filed Feb. 26, 1990, by the assignee, G.D. Searle & Co., Ltd.

Hereby disclaims and dedicates to the Public the remaining term of said patent.
[*Official Gazette September 25, 1990* ]